United States Patent
Neuman

(10) Patent No.: US 6,889,689 B1
(45) Date of Patent: May 10, 2005

(54) BUBBLE CPAP CAP FOR NEONATES

(76) Inventor: Deborah W. Neuman, 4301 Milton Ave., Camillus, NY (US) 13031

( * ) Notice: Subject to any disclaimer, the term of this patent is extended or adjusted under 35 U.S.C. 154(b) by 0 days.

(21) Appl. No.: 10/752,069

(22) Filed: Jan. 6, 2004

(51) Int. Cl.$^7$ .............................................. A62B 18/00
(52) U.S. Cl. .............................. 128/201.22; 128/207.18
(58) Field of Search ...................... 128/201.22, 201.29, 128/201.24, 203.22, 204.11, 205.25, 206.11, 128/206.27, 207.11, 207.13, 207.17, 207.18, 128/DIG. 26; 2/171, 171.5, 172, 173, 209.13

(56) References Cited

U.S. PATENT DOCUMENTS

| | | | |
|---|---|---|---|
| 4,367,735 A | 1/1983 | Dali ........................ | 128/207.18 |
| 4,406,283 A | 9/1983 | Bir ........................... | 128/207.18 |
| 4,485,495 A * | 12/1984 | Lunt .......................... | 2/200.1 |
| 4,593,688 A * | 6/1986 | Payton ................... | 128/200.28 |
| 4,641,647 A * | 2/1987 | Behan .................... | 128/207.18 |
| 4,665,566 A | 5/1987 | Garrow .......................... | 2/171 |
| 4,774,946 A | 10/1988 | Ackerman et al. ..... | 128/207.18 |
| 4,808,160 A * | 2/1989 | Timmons et al. ........ | 604/94.01 |
| 5,188,101 A * | 2/1993 | Tumolo ................. | 128/207.18 |
| 5,517,986 A | 5/1996 | Starr et al. ............... | 128/206.4 |
| 5,542,128 A * | 8/1996 | Lomas ........................... | 2/173 |
| 5,645,058 A * | 7/1997 | Odom ................... | 128/207.18 |
| 6,684,883 B1 * | 2/2004 | Burns .................... | 128/207.18 |
| 2003/0034030 A1 | 2/2003 | Carlucci et al. ....... | 128/200.24 |
| 2003/0047185 A1 | 3/2003 | Olsene t al. .......... | 128/203.22 |
| 2003/0145859 A1 * | 8/2003 | Bohn et al. ............ | 128/206.24 |
| 2004/0083534 A1 * | 5/2004 | Ruiz et al. .................... | 2/171.2 |

* cited by examiner

Primary Examiner—Henry Bennett
Assistant Examiner—Teena Mitchell
(74) Attorney, Agent, or Firm—Bernhard P. Molldrem, Jr.

(57) ABSTRACT

A neonatal cap is adapted to secure CPAP breathing air tubes to the infant's head. A fabric cap covers the infant's forehead, the top and back of the infant's head, and left and right temples and ears. Left and right lower flaps extend downward from temple portions of the cap below the infant's jaw, and a releasable chin strap passes below the infant's jaw to secure the ends of the left and right lower flaps to one another. Left and right hook-and-loop temple straps are used for securing the air tubes, and each includes a hook fabric portion affixed onto a respective temple portion of the cap and an associated loop fabric strip secured at one end to the cap at the respective temple portion. The rear of the cap is free of seams, for comfort.

8 Claims, 4 Drawing Sheets

BUBBLE CPAP CAP FOR NEONATES

BACKGROUND OF THE INVENTION

This invention relates to devices for providing breathing assistance to neonatal infants, in is more particularly concerned with headwear, i.e., a neonatal cap, that can be used to hold breathing air tubes that lead to a nasal cannula.

Hospital care for neonatal infants frequently requires supplemental oxygen be provided. This typically involves the use of a nasal cannula, in which a transverse air tube has a pair of prongs that enter the infant's nares and provide breathing gases under positive pressure. Positive pressure is used to maintain the infant's airways, and the apparatus is known as continuous positive airway pressure, or CPAP. The breathing gases are provided from a source located near the infant's crib, and pass through a pair of flexible hoses or conduits to the cannula, which is located beneath the infant's nose. The source, which provides the breathing gases at a low volume, is often called a Bubble CPAP machine. It is common to hold the breathing apparatus in place on the infant's head by use of safety pins that are inserted into a knit neonatal cap that the infant is wearing, with the safety pins each holding one of the two flexible hoses.

In this system, if there is a detected sudden pressure change in the breathing gases, an alarm sounds to alert a pediatric nurse to a potential breathing problem with the child. Unfortunately, normal movements of the infant can sometimes cause the cannula to move away from the nose, which triggers the alarm. Also, unless the infant's jaw or chin is gently restrained, it is possible that the infant will begin mouth breathing, which also causes a change in ventilation pressure and can sound an alarm.

An arrangement for clamping the air delivery tubes to the infant's head is described in Ackerman et al. U.S. Pat. No. 4,774,946. In that arrangement, a headband is placed around the child's head, and a pair of rigid yokes, placed on the headband, each hold one of the air tubes. These rigid yokes can cause discomfort or injury to the neonatal infant if they should slip out of place.

A tubular knit head band for neonatal use has been proposed in Published Appln. No. US 2003/0034030 to Carlucci et al. In that approach, there is an elastic knit band that goes over the forehead and back of the infant's head, and a pair of integrated loops attached to the headband, so that each of the two air tubes or hoses is positioned in one of the integrated loops. This approach does have the advantage of being made of soft material. However, the entire headband can slip off the infant's head from normal movement, and there is no thought given to urging the infant's mouth closed to discourage mouth breathing. In addition, the two hoses have to be slipped endwise into the two integrated loops, as they are not provided with any means for closing and opening to receive the air tubes from the side.

Neonatal caps are often used in newborn care facilities to prevent too much body heat from escaping from the infant through exposed regions of the head. Frequently, knit fabric is used. The crown, forehead, and back of the infant's head is covered to prevent too much heat loss. A disposable cap for neonatal infants is discussed in U.S. Pat. No. 4,485,495.

OBJECTS AND SUMMARY OF THE INVENTION

Accordingly, it is an object of the present invention to provide a head cover suitable for neonatal infants, and provided with means for securely holding the hoses or tubes that carry breathing gases to a nasal cannula, and which provides comfort and avoids the drawbacks of the prior art.

It is another object to provide a neonatal cap that is made of soft materials and which can fit comfortably and snugly on the infant.

It is a more specific object to provide a neonatal cap that is made without seams at the back of the head to provide increased comfort to the infant.

Another object is to provide a cap that is secured gently under the chin to discourage the infant from breathing through the mouth, and so that the cap is held more securely in place.

A further object is to provide the cap with hook-and-loop fabric strips, e.g., Velcro, at left and right temples of the cap to hold the breathing gas supply tubes comfortably in place.

A still further object is to cushion and cover the neonatal infant's ears to soften noise from air flow in the breathing gas tubes.

In accordance with one aspect of the present invention, neonatal headwear provided for a newborn infant includes means for securing a pair of breathing air tubes. The headwear is in the form of a fabric cap that covers the forehead of the infant's head above the face, the top of the infant's head, back of the head, and left and right temples and ears. There are also left and right lower flaps that extend downward from the temple portions of the cap below the infant's jaw. A chin strap passes below the infant's jaw in front of the neck and secures the ends of the left and right lower flaps to one another, so the cap is held comfortably in place on the infant's head. The means for securing the air tubes can be in the form of left and right hook-and-loop (e.g., Velcro) temple straps. Each of these favorably has a hook fabric portion affixed onto the respective (left or right) temple portion of the cap and also has an associated loop fabric strip secured at one end to the cap at the respective temple portion. Preferably, the loop fabric strip is sewn to the cap at one end at the corresponding end of the hook material, so that it overlies the hook material portion. The loop fabric strip may favorably be about 25% longer than the hook fabric, as it has to accommodate the thickness of the air tube. Other non-rigid securement arrangements could be used for the temple straps. The cap may be sewn in a way that avoids having any seams at the back of the head, to avoid discomfort to the neonatal infant. Preferably, the upper part of the cap, i.e., the forehead, crown, back and temple portions, can be sewn from a unitary soft cloth blank, with one seam formed medially at the center of the forehead portion and extending only partway across the crown portion, so as to avoid any seam at the back of the head. The lower chin flaps may be part of this unitary piece, or may be separate pieces sewn on.

The cap may be made of a suitable knit or woven cloth that is soft and pliable, and preferably which may be laundered and sanitized for repeated use.

The above and many other objects, features, and advantages of this invention will be more fully appreciated from the ensuing description of a preferred embodiment, which is to be read in conjunction with the accompanying Drawing.

DETAILED DESCRIPTION OF THE PREFERRED EMBODIMENT

Figure 1:
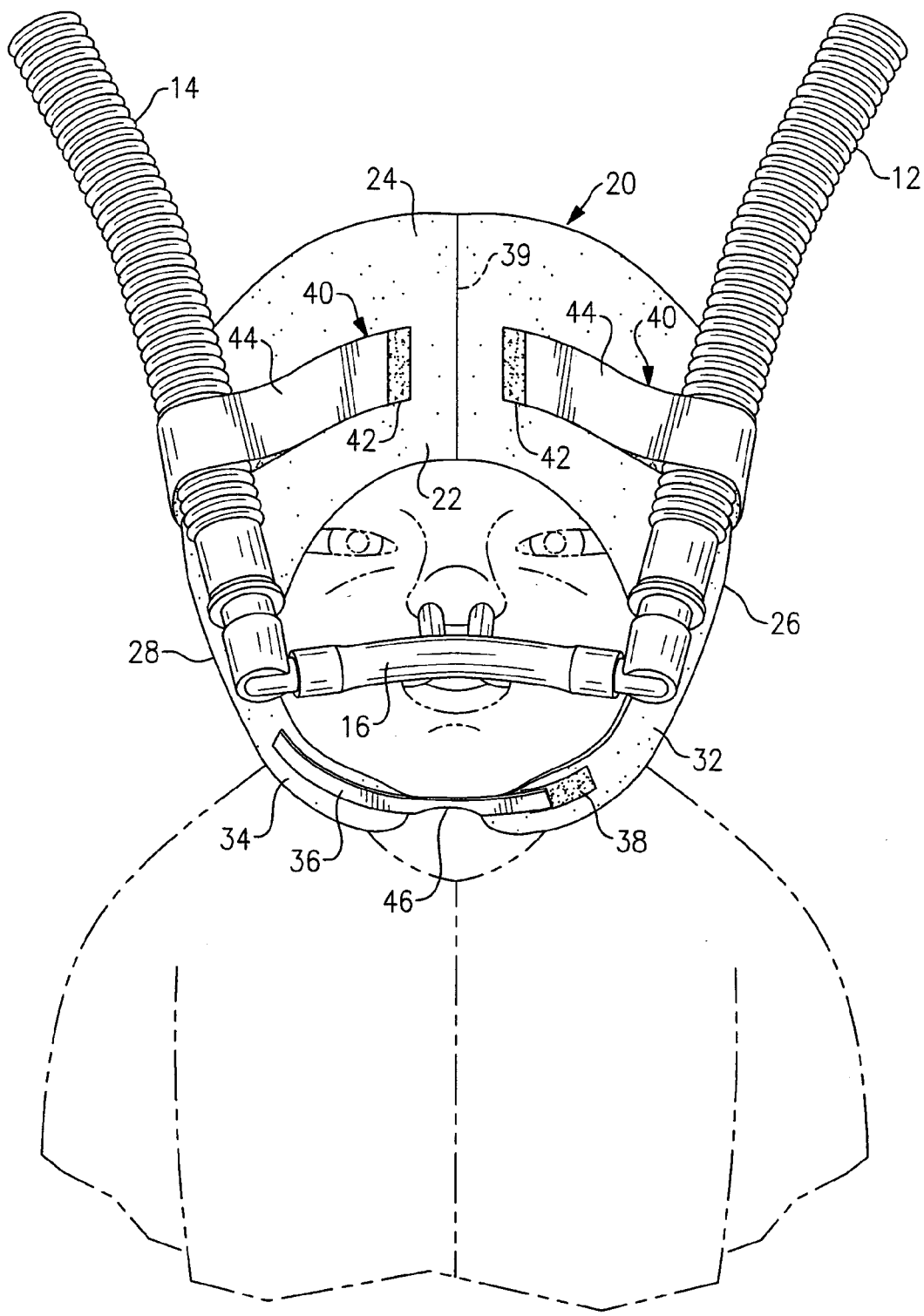
FIG. 1 is a frontal view of a neonatal cap according to an embodiment of the present invention, being worn by an infant (shown in ghost lines), and provided with straps for holding the breathing gas supply lines of a Bubble CPAP arrangement.

With reference now to the Drawing, FIG. 1 shows a bubble CPAP arrangement for an infant, in which breathing gases are supplied from a source (not shown), through a pair of tubes or hoses 12, 14 to a nasal cannula 16 that is fitted against the nares of the infant. A neonatal cap 20 here plays the dual role of preventing excessive heat loss and also holding the air hoses 12 and 14 properly in position.

The cap 20 is made of a soft pliable cloth fabric, which may be woven or knit. In this embodiment a combed cotton fabric is used, as it exhibits a high degree of wearer comfort. The material can also be easily laundered and kept clean and sanitary. The fabric can be a plain color or can be a cheerful print design.

Figure 2:
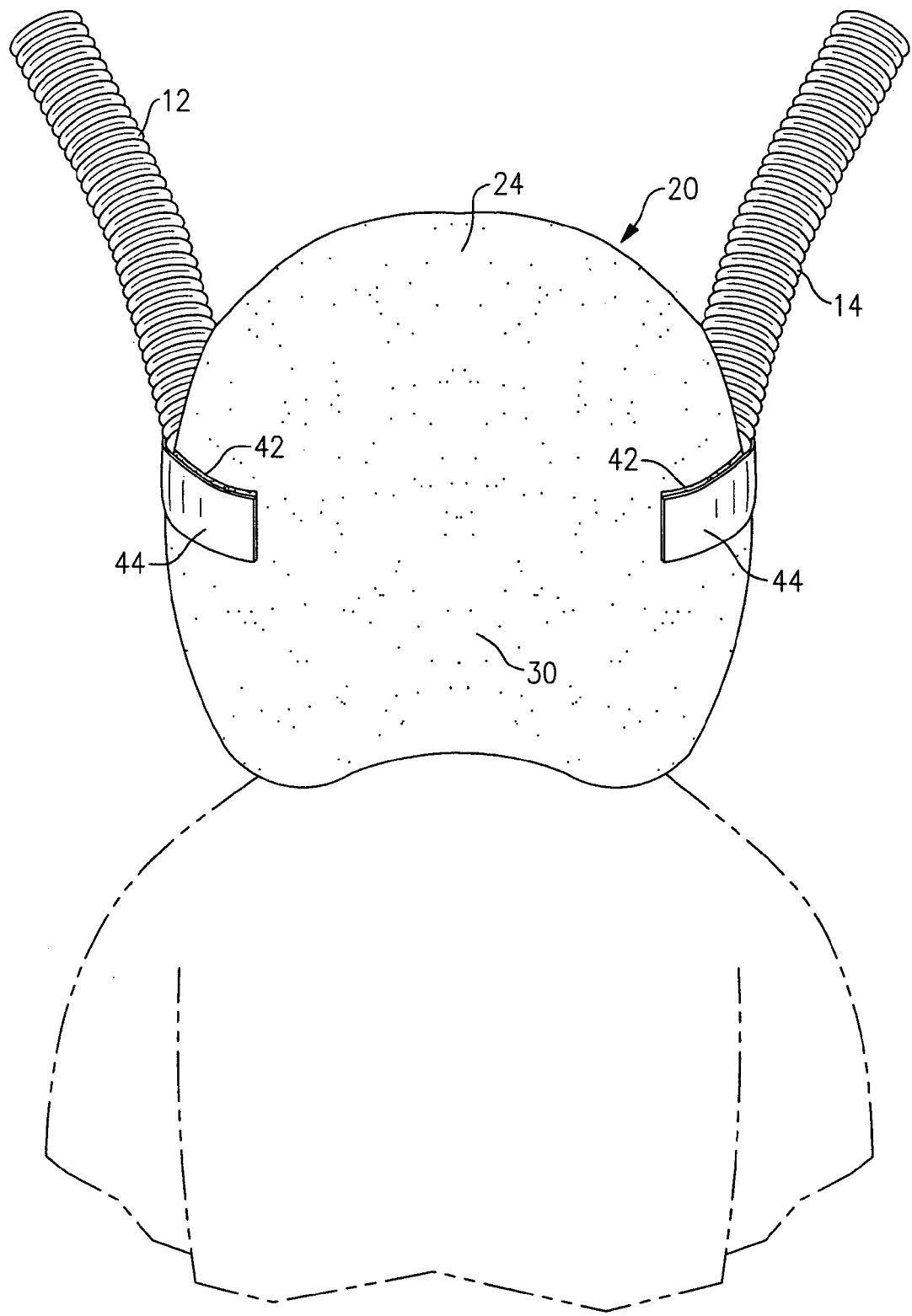
FIG. 2 is an back view of this embodiment.
Figure 3:
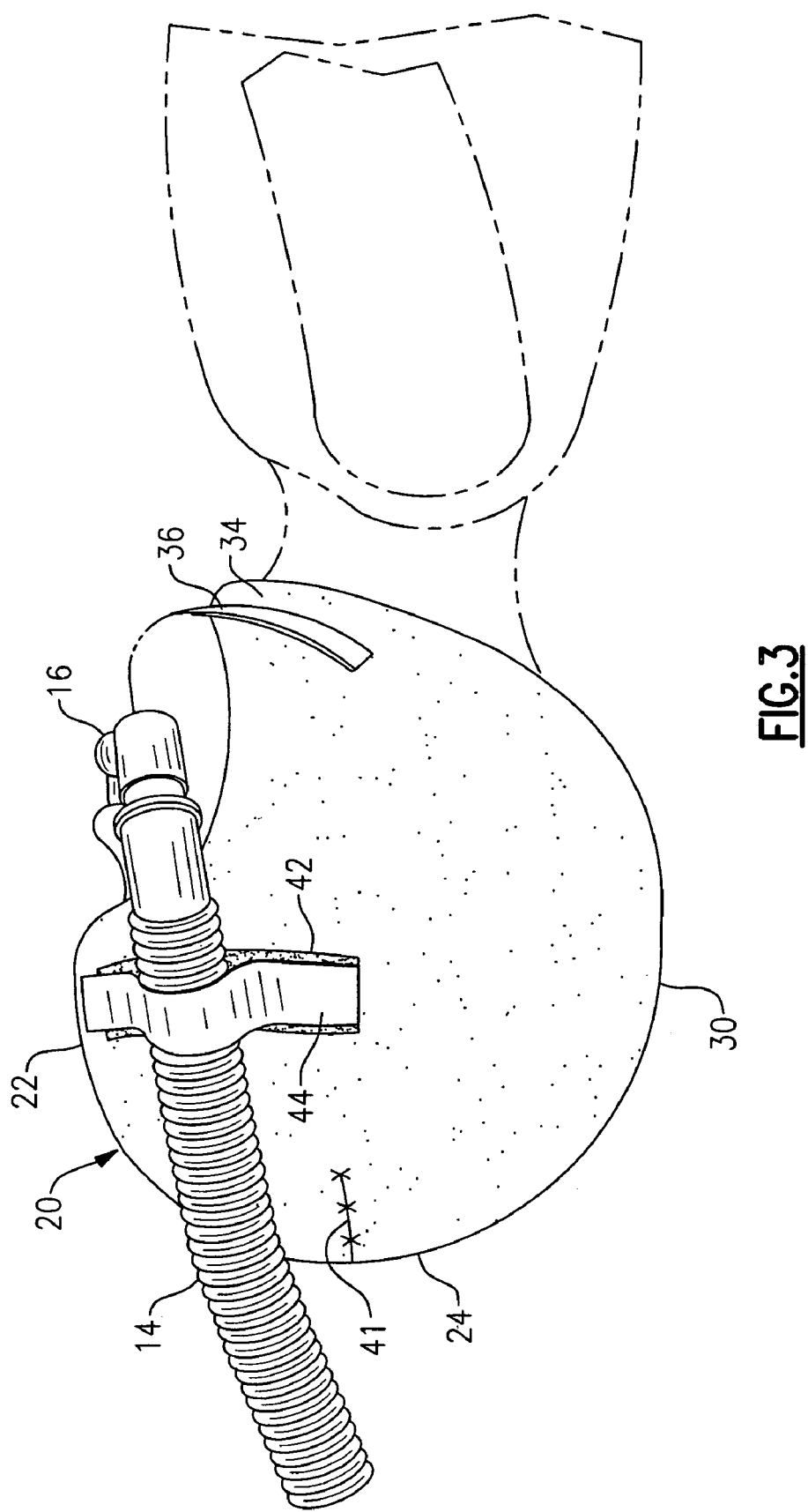
FIG. 3 is a left side elevation of this embodiment.
Figure 4:
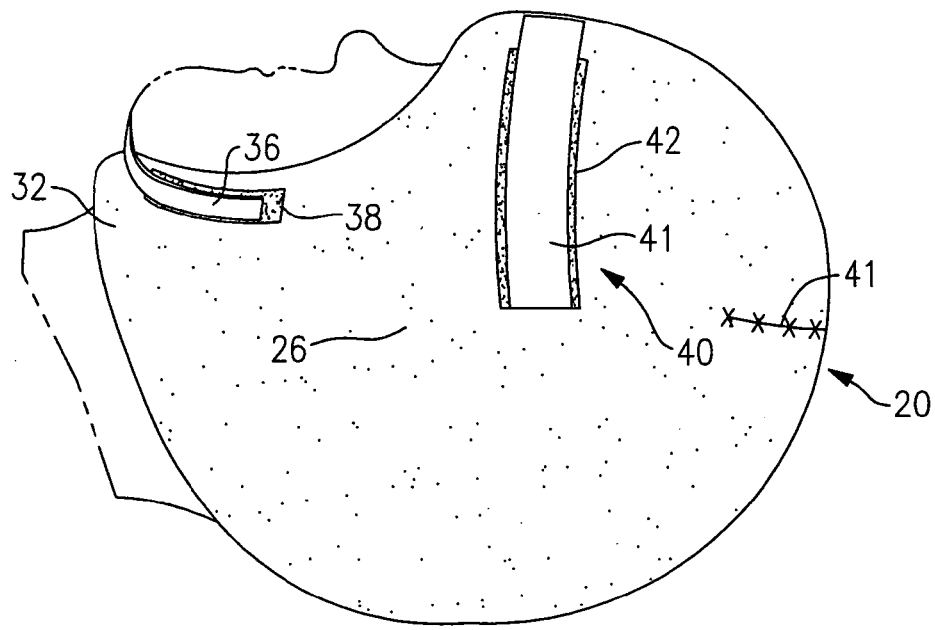
FIG. 4 is a right side elevation but without the associated air tube.

As shown also in FIGS. 2, 3, and 4, the cap 20 fits closely on the head of the infant, and has a forehead portion 22 that covers the infant's forehead above the eyes, a crown portion 24 that covers the top of the head, left and right temple portions 26 and 28 that extend over the temples and ears of the infant, and a back 30 that extends from the rear of the crown portion 24 down to the infant's neck. There are left and right lower flaps 32 and 34 that taper down and end below the infant's lower jaw. A chin strap 36 is sewn at one end to the one lower flap 34 (FIG. 3). There is a patch 38 of Velcro or another similar hook-and-loop type fastener material affixed onto the other lower flap 32 (FIG. 4), and a strip of mating fastener material on the chin strap 36 releasably fastens to it. The mating fastener material on the chin strap is obscured in this view. This arrangement allows the cap 20 to be tightened snugly, but comfortably, by adjusting the chin strap.

Figure 5:
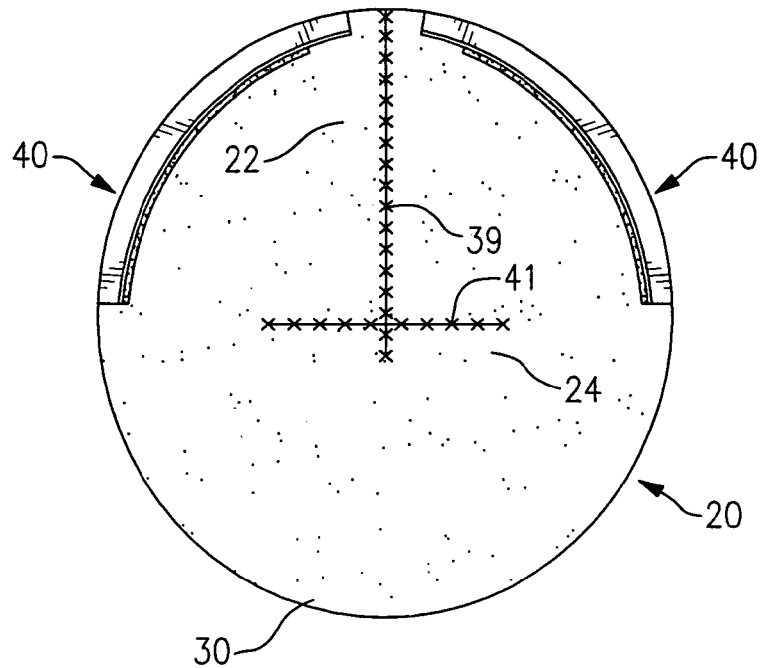
FIG. 5 is a top view of the cap of this embodiment.

As shown in FIGS. 1, 2, and 5, there is a central seam 39 that is located medially on the forehead portion 22 of the cap 20, and this seam 39 extends into the crown portion 24, terminating there. A small transverse seam 41 across the top helps the cap 20 contour to the head. This construction leaves the back portion 30 free of any sewn seams, optimizing comfort for the infant. Neonatal care requires that the infants rest only on their backs, so the back of the head is always subject to some pressure.

Hold-downs 40 for the air hoses or tubes 12, 14 are affixed onto the forehead portion 22 and left and right temple portions 26, 28 of the cap. In each case, the hold-down 40 preferably employs a temple strap formed of a strip 42 of the stiff, hook portion of hook-and-loop closure material, such as Velcro, extending laterally from near the seam 39. In this embodiment, the strips 42, 42 are about three inches in length. Strips 44, 44 of flexible mating loop-type material are sewn at one end to a position on the cap corresponding to the outside or back end of the corresponding strip 42, so that the upper, loop-type strip 44 overlies the under, hook-type strip 42. The upper strips 44 are slightly longer than the under strips 42, in this embodiment about three-and-three-quarters inches, so as to accommodate the thickness of the hose or air tube. FIG. 4 illustrates the cap 20 without the air hose, and with the upper strip 44 overlying and extending beyond the end of the under strip 42. The actual dimensions depend on the size of the neonatal infant, and can vary from what is used in this embodiment. The neonatal care center of the hospital would be provided with a supply of various sizes of caps 20.

A curved cutout 46 is formed on the neck side of the chin strap 36; that is, a small amount of the material has been trimmed away on the neck side to avoid some chafing of the infant's neck.

In other embodiments, one or both of the lower flaps 32, 34 can extend all the way across the neck to the other lower flap, to that the flaps meet, and themselves serve as chin strap.

In this embodiment, the cap 20 can be formed from a unitary blank of material, and with the only seam being that seam 39 that is at the forehead and crown portions. In other embodiments, the flaps 32, 34 could be separate cloth panels that are sewn onto the temple portions.

In this embodiment, the cap 20 exposes only the face of the infant's head, and covers the infant's ears. This reduces the noise level from the CPAP apparatus that the infant experiences.

The chin strap 36 or other equivalent means for securing the cap under the infant's jaw ensures a snug comfortable fit, so that movement of the infant or of the hoses will not cause the nasal cannula 16 to slip away from the infant's nose. The use of Velcro or similar materials for the hold-downs 40, 40 ensure that the hoses 12 and 14 are held more securely than is the case for tied arrangements, such as laces, and also avoids the need for safety pins or other sharp objects near the infant. The infant's mouth is gently urged to stay closed, by virtue of the chin strap 36. Thus, the use of this cap 20 decreases instances of alarming, and ensures that the CPAP works the way it is designed to work.

The materials used in the cap 20 are launderable and can be washed and sterilized as needed so that the cap 20 can be re-used again and again.

While the invention has been described with reference to a specific preferred embodiment, the invention is certainly not limited to that precise embodiment. Rather, many modifications and variations will become apparent to persons of skill in the art without departure from the scope and spirit of this invention, as defined in the appended claims.

I claim:

1. Neonatal headwear for a newborn infant including means for securing a pair of breathing air tubes, the headwear comprising a fabric cap adapted to cover a forehead of an infant's head above the eyes and nose, a top of the infant's head, back of the infant's head, and left and right temples and ears; the cap including left and right lower flaps that extend downward from temple portions of the cap below the infant's jaw; and releasable chin strap means passing below the infant's jaw for securing ends of the left and right lower flaps to one another; and the means for securing comprising left and right temple straps each affixed onto a respective temple portion of the cap and which can be secured around a respective one of said breathing air tubes.

2. Neonatal headwear according to claim 1 wherein said chin strap means includes a chin strap having a curved recess on a neck-facing side thereof.

3. Neonatal headwear according to claim 1 wherein said chin strap means includes a hook-and-loop releasable material having one portion secured to one of the lower flaps and a mating portion secured to the other lower flaps.

4. Neonatal headwear according to claim 1 wherein each of said temple straps includes a hook fabric portion affixed onto a respective temple portion of the cap, and an associated loop fabric strip secured at one end to the cap at the respective temple portion.

5. Neonatal headwear according to claim 4 wherein each said temple strap hook fabric portion is a strip of hook fabric affixed to the cap, and the associated loop fabric strip is secured at one end to an end of the hook fabric strip.

6. Neonatal headwear according to claim 5 wherein said strip of loop fabric is about 25% longer than the associated hook fabric strip.

7. Neonatal headwear according to claim 1 wherein said cap is free of seams on the portion of the cap that covers the back of the infant's head.

8. Neonatal headwear according to claim 7 wherein the portions of the cap that cover the forehead, top, temples, and back of the infant's head are sewn from a unitary blank of fabric, employing a seam that extends medially across a forehead portion of the cap and continues partway across a crown portion of the cap, but terminates before reaching a back of the cap, so that the back of the cap is free of seams where the cap contacts the back of the infant's head.

* * * * *